(12) United States Patent
Scott

(10) Patent No.: US 10,914,666 B2
(45) Date of Patent: Feb. 9, 2021

(54) APPARATUS AND METHOD FOR VALIDATING THE OPERATION OF A PPM ANALYZER

(71) Applicant: Phase Dynamics, Inc., Richardson, TX (US)

(72) Inventor: Bentley N. Scott, Garland, TX (US)

(73) Assignee: Phase Dynamics, Inc., Richardson, TX (US)

( * ) Notice: Subject to any disclaimer, the term of this patent is extended or adjusted under 35 U.S.C. 154(b) by 141 days.

(21) Appl. No.: 16/358,122

(22) Filed: Mar. 19, 2019

(65) Prior Publication Data

US 2019/0285533 A1 Sep. 19, 2019

Related U.S. Application Data

(60) Provisional application No. 62/644,918, filed on Mar. 19, 2018.

(51) Int. Cl.
| | |
|---|---|
| *G01N 15/06* | (2006.01) |
| *G01N 5/02* | (2006.01) |
| *G01N 33/18* | (2006.01) |

(52) U.S. Cl.
CPC ........... *G01N 15/0631* (2013.01); *G01N 5/02* (2013.01); *G01N 33/18* (2013.01)

(58) Field of Classification Search
CPC .. G01N 15/0631; G01N 33/18; G01N 33/225; G01N 5/02; G01N 5/025
See application file for complete search history.

(56) References Cited

U.S. PATENT DOCUMENTS

| 2012/0182546 A1* | 7/2012 | Chaouki | G01N 21/3563 356/73 |
| 2015/0003582 A1* | 1/2015 | Polikhov | G01N 23/12 378/53 |

\* cited by examiner

*Primary Examiner* — Suman K Nath

(57) ABSTRACT

A system comprising a parts-per-million (PPM) analyzer configured to analyze a multiphase fluid, the fluid comprising water. The analyzer includes a mesh comprising first adsorbent materials that adsorb specific substances from the multiphase fluid. The system includes a mass meter configured to measure a mass of multiphase fluid passing through the PPM analyzer; a molecular sieve dryer comprising second adsorbent material configured to adsorb the water from the multiphase fluid; and a plurality of valves configured to couple the mass meter and the molecular sieve dryer to the PPM analyzer. During routine operation, the valves direct the multiphase fluid through the PPM analyzer. During a validation operation, the valves divert the multiphase fluid through the molecular sieve dryer prior to entering the PPM analyzer.

8 Claims, 5 Drawing Sheets

APPARATUS AND METHOD FOR VALIDATING THE OPERATION OF A PPM ANALYZER

CROSS-REFERENCE TO RELATED APPLICATION(S) AND CLAIM OF PRIORITY

The present application is related to U.S. Provisional Patent No. 62/644,918, filed Mar. 19, 2018, entitled "PPM Analyzer Validation Method". Provisional Patent No. 62/644,918 is assigned to the assignee of the present application and is hereby incorporated by reference into the present application as if fully set forth herein. The present application hereby claims priority under 35 U.S.C. § 119(e) to U.S. Provisional Patent No. 62/644,918.

TECHNICAL FIELD

The present application relates generally to apparatuses and methods for validating an analyzer for the amount of water at parts-per-million (PPM) levels in a condensate.

BACKGROUND

The measurement of water levels in the parts-per-million (PPM) range in gas condensate is important due to the formation of hydrates, which can block a pipeline and potentially create a rupture if the levels are not kept below 250 PPM. When crude oil containing water is pumped from underground to the surface of the earth, water is removed from the liquid gas condensate during refinement through processes having 3-5 steps. The steps may include bulk water removal, cooling, and coalescing. The accurate determination of water content in a liquid gas condensate may help in preventing potentially hazardous hydrate formation in the pipelines. This is especially important in cold climates, such as Canada and for offshore platforms where the pipeline sends the liquids to shore through a subsea pipeline. If a rupture occurs due to hydrate formation, the expense and damage may be great.

Refining processes typically use real-time, online water measurement analyzers to determine the PPM level of water in liquid condensates. One exemplary real-time, online water measurement analyzer is disclosed in U.S. Pat. No. 6,630,833, which is hereby incorporated by reference as if fully set forth herein. However, the accuracy of the real-time water measurement analyzers must be verified periodically by an offline sample testing apparatus that separately tests the water content of a sample of liquid condensate to confirm the measurements made by the real-time, online water measurement analyzer. Such an offline method involves physically sampling the stream and analyzing it in a laboratory setting.

However, one problem with the offline method is that the liquid gas condensate evaporates due to the high vapor pressure of the liquid, therefore biasing the sample. In addition, since the amount of water is at PPM levels, only a titration laboratory determination of water may be processed. Titration in the laboratory is highly dependent upon the operator and sample handling. The object of titration is to collect a sample that is representative of the entire process stream, while pulling a sample size of less than 1 milliliter. Typically, the sample is captured in a small section of line with valves on both sides and easy-to-disconnect fittings in between. When the sample is captured and the fittings are separated, the water may condense from the atmosphere due to the cooling effect caused by "flashing" of the condensate left in the fitting. During flashing, the container cools due to the expansion of the liquids into gas and ambient air water vapor may easily condense on the surfaces. This small amount of condensed water may enter the titration apparatus, thereby biasing the measurement. Other techniques to determine PPM levels of water are also affected by flashing and liquid condensate-to-gas transitions before making an accurate measurement.

Therefore, there is a need in the art for improved methods and apparatuses of accurately determining the amount of water in a sample of a liquid condensate extracted from a petroleum processing pipeline. In particular, there is a need for improved methods and apparatuses of accurately determining the amount of water in the parts-per-million (PPM) range in a liquid condensate that are not affected by the extraction process or by changes in temperature and pressure during the testing process.

SUMMARY

To address the above-discussed deficiencies of the prior art, it is a primary object to provide, a system comprising: i) a parts-per-million (PPM) analyzer configured to analyze a multiphase fluid, the fluid comprising water, wherein the analyzer includes a mesh comprising first adsorbent materials that adsorb specific substances from the multiphase fluid; ii) a mass meter configured to measure a mass of multiphase fluid passing through the PPM analyzer; iii) a molecular sieve dryer comprising second adsorbent material configured to adsorb the water from the multiphase fluid; and iv) a plurality of valves configured to couple the mass meter and the molecular sieve dryer to the PPM analyzer, wherein during routine operation, the valves direct the multiphase fluid through the PPM analyzer and wherein during a validation operation, the valves divert the multiphase fluid through the molecular sieve dryer prior to entering the PPM analyzer.

In one embodiment, the mass meter comprises a Coriolis meter.

In another embodiment, the second adsorbent material in the molecular sieve dryer has a known mass and adsorbs a known mass of water when saturated.

In still another embodiment, the system further comprises a system controller configured to determine a zero reference point in an output of the analyzer, the zero reference point indicating that during the validation operation, the multiphase fluid from the molecular sieve dryer has removed substantially all of the water associated with the first adsorbent materials in the mesh.

In yet another embodiment, the system controller is further configured to determine a saturation point in the output of the analyzer, the saturation point indicating that during the validation operation, the second adsorbent material associated with the molecular sieve dryer has become saturated.

In a further embodiment, the system controller uses the known mass of water when the second adsorbent material is saturated to verify the parts-per-million of water that passed through the PPM analyzer during the validation operation.

It is another primary object to provide a method of validating the operation of a parts-per-million (PPM) analyzer configured to analyze a multiphase fluid, the fluid comprising water, the method comprising: i) during a routine operation, directing the multiphase fluid through the PPM analyzer, wherein the analyzer includes a mesh comprising first adsorbent materials that adsorb specific substances from the multiphase fluid; ii) during a validation operation, diverting the multiphase fluid through a molecular sieve prior to entering the PPM analyzer, the molecular sieve comprising a second adsorbent material that adsorbs the water from the multiphase fluid; iii) measuring the mass of multiphase fluid passing through the PPM analyzer during the validation operation; and iv) determining a zero reference point in an output of the analyzer, the zero reference point indicating that during the validation operation, the multiphase fluid from the molecular sieve dryer has removed substantially all of the water associated with the first adsorbent materials in the mesh.

In one embodiment, the method further comprises determining a saturation point in the output of the analyzer, the saturation point indicating that during the validation operation, the second adsorbent material associated with the molecular sieve dryer has become saturated.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

FIGS. 1 through 5, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged multiphase fluid processing system.

The present application is related to the apparatus and method described in U.S. patent application Ser. No. 15/710, 551, entitled "Apparatus And Method For Validating Water Level In Condensate Measurement," filed on Sep. 20, 2017. Application Ser. No. 15/710,551 is assigned to the assignee of the present application and is hereby incorporated by reference into the present application as if fully set forth herein.

Figure 1:
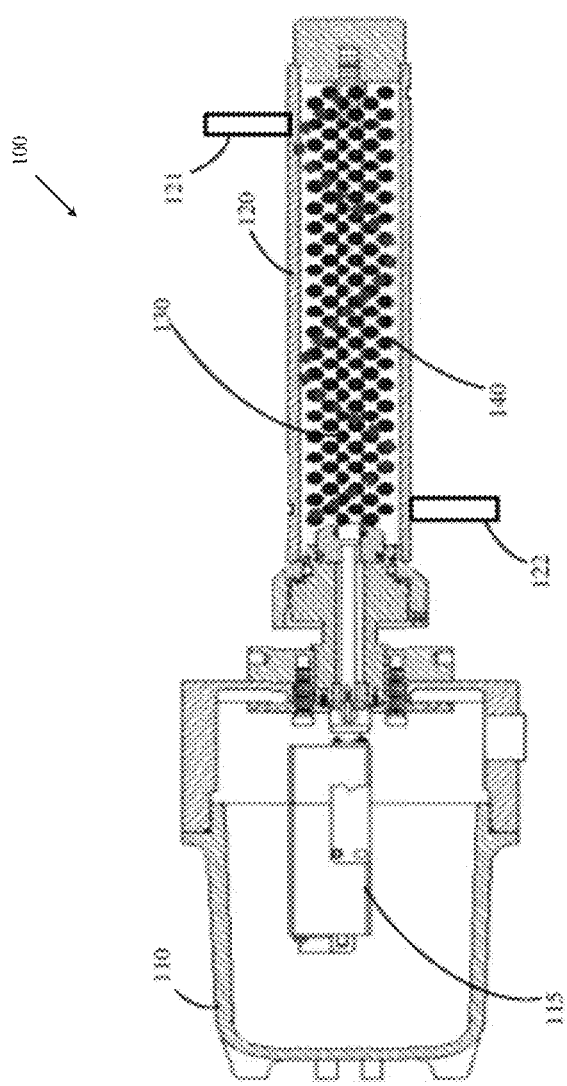
FIG. 1 illustrates an analyzer used in a method to measure PPM levels of water in hydrocarbon fluids and gases according to an embodiment of the disclosure.

FIG. 1 illustrates analyzer 100, which is used in a method to measure parts-per-million) PPM levels of water in hydrocarbon fluids and gases according to an embodiment of the disclosure. U.S. Pat. No. 6,630,833 to Scott discloses similar apparatuses and related methods. U.S. Pat. No. 6,630,833 was incorporated by reference above as if fully set forth herein.

Analyzer 100 comprises housing 110, electronics module 115, pipe section 120, inlet 121, outlet 122, probe 130, and a plurality of adsorbent beads 140. A metal mesh confines the adsorbent beads 140. A multiphase fluid or gas flows into inlet 121, through the interior of pipe section 120, and exits via outlet 122. Electronics module 115 and probe 130 (typically an antenna) generate an electronic waveform having a characteristic (e.g., frequency) that changes as a property (e.g., permittivity) of the multiphase fluid or gas changes. In general, the multiphase fluid comprises a low polar moment solvent with entrained solution water and free water.

Beads 140 are selected to adsorb particular materials. The mesh allows the stream of liquid or gas to pass through pipe section 120, so that beads 140 are able to adsorb the material in the liquid or gas media to which beads 140 are specific. This changes, for example, the permittivity of the multiphase (liquid and/or gas) fluid in which the electromagnetic field is propagating. As explained in U.S. Pat. No. 6,630, 833, electronics module 115 detects the change in permittivity using classical microwave methods, such as phase shift, amplitude changes, frequency changes in a cavity, the frequency of an unbuffered oscillator, and the like. Some embodiments may use a two-cylinder structure, where an outer cylinder contains a material that selectively removes a contaminant chemical that may be interferes with the sensing of a desired chemical. The outer cylinder does not play a part in the measurement because it is outside the metal shield which contains the measurement adsorbent, and is thus outside the electromagnetic field.

Beads 140 in pipe section 120 have free surface without metallization. Inlet 121 becomes a filter and the area of measurement is relatively large. The sensitivity is determined by the microwave frequency of the oscillator circuitry in electronics module 115. The length of pipe section 120 is one factor that determines how fast changes are seen and the sensitivity of the apparatus. Analyzer 100 becomes a monitor for determining when the drying bed molecular sieves are fully saturated with water.

Validation of the operation of analyzer 100 is important for several reasons. A microwave analyzer with $AL_2O_3$ medium requires validation in-line at process conditions to satisfy pipeline companies and co-producers. Conventional methods to validate are typically very uncertain. Measurement errors of up to 50% may occur during sampling and titration. Often, interfering with a real-time process is expensive and highly uncertain. Additionally, it is preferable not to send entrained water to the pipeline.

Figure 2:
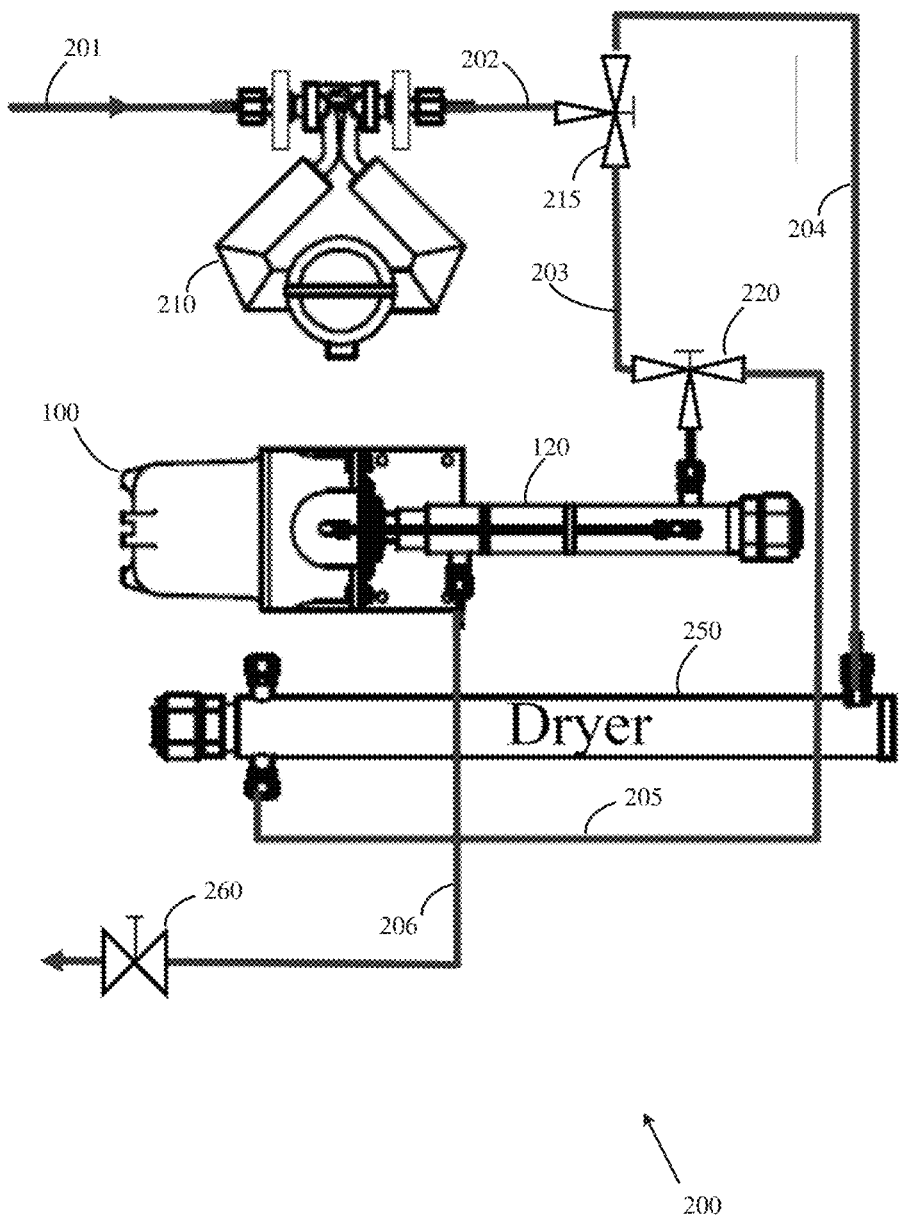
FIG. 2 illustrates a system for verifying the operation of the parts-per-million (PPM) analyzer of FIG. 1 according to an embodiment of the disclosure.

FIG. 2 illustrates system 200 for verifying the operation of parts-per-million (PPM) analyzer 100 of FIG. 1 according to an embodiment of the disclosure. System 200 comprises conduits 201-206, Coriolis meter 210, two-way valve 215, two-way valve 220, molecular sieve dryer 250, and valve 260. System 200 includes Coriolis meter 210 in order to accurately determine the flow and density of the multiphase (liquid and/or gas) fluid that is flowing through pipe section 120 of analyzer 100.

Molecular sieve dryer 250 verifies a zero threshold of water in gas and/or fluid media. Two-way valves 215 and 220 switch dryer 250 in and out of the flow path of the multiphase fluid that passes through pipe section 120. In routine on-line operation, valves 215 and 220 are configured so that the multiphase fluid flows into conduit 201, through Coriolis meter 210, which measures the density and mass of the multiphase fluid. The multiphase fluid then flows from Coriolis meter 210 into conduit 202, through valve 215, into conduit 203, and through valve 220 into pipe section 120. The permittivity (or other property) of the multiphase fluid is measured in pipe section 120 before flowing into conduit 206 and out of valve 260. This provides a means to determine when the molecular sieve drying bed becomes saturated.

However, the accuracy of analyzer 100 may be validated by switching valve 215 and 220 so that the multiphase fluid is first diverted through molecular sieve 250. In this method, the multiphase fluid flows into conduit 201, through Coriolis meter 210, which measures the density and mass of the multiphase fluid. The multiphase fluid then flows from Coriolis meter 210 into conduit 202, and is diverted by valve 215 into conduit 204, and then into the inlet of dryer 250. The multiphase fluid flows through dryer 250, into conduit 205, and then into valve 220, which sends the multiphase fluid into pipe section 120. The permittivity (or other property) of the multiphase fluid is measured in pipe section 120 before flowing into conduit 206 and out of valve 260.

According to one embodiment of the present disclosure, analyzer 100 comprises an internal system controller (not shown) that may be, for example, a processor or microcontroller on electronics module 115. The internal system controller communicates with, and reads data from, Coriolis meter 210 and controls the settings of valves 215 and 220. The internal system controller also performs the test runs and validation procedures described herein and calculates, among other things, the zero PPM point, the saturation point, and polynomial equations described below. In an alternate embodiment, the system controller may comprise an external stand-alone controller that communicates with and controls analyzer 100, Coriolis meter 210 and valves 215 and 220. However, for the sake of simplicity and brevity, it will be assumed that the system controller is implemented on electronics module 115 in analyzer 100.

Molecular sieve dryer 250 adsorbs the water molecules (free or in solution) in the multiphase fluid and must be heated to 200-300 degrees Celsius for regeneration or release of the water molecules to occur. If the process is dry enough, molecular sieve dryer 250 will adsorb 100% of the water going to analyzer pipe section 120 before it becomes fully saturated with water. This point becomes the zero PPM level for analyzer 100 as pipe section 120 only sees dry liquids. The corresponding inflection point seen in analyzer 100 response will show when the molecular sieve in dryer 250 becomes saturated. If the process is high enough in water to prevent this from occurring before the molecular sieve becomes saturated, then an inflection point will still be seen in the analytical response of analyzer 100.

Molecular sieve dryer 250 contains a precisely known mass of adsorbent beads. Since the amount of water that can be adsorbed by a given mass of adsorbent beads is also known, the starting mass of dry beads and the final mass of saturated beads may be use to calculate the exact amount of water that is adsorbed during the flow of multiphase fluid through dryer 250. By way of example, dryer 250 may be filled with 1 kilogram of dry adsorbent beads (e.g., aluminosilicate crystalline or zeolites) that adsorb 22% of their mass in water. Therefore, when the adsorbent material reaches a mass of 1.22 kilograms, the adsorbent material is saturated and will adsorb no more water. The amount of water removed from the multiphase fluid will be 0.22 kilograms.

In this manner, the molecular sieve may verify operation of analyzer 100 and calibrate the zero PPM point. Molecular sieve dryer 250 may also be used to back-calculate an approximate PPM loading. This requires measurement by Coriolis meter 210 of the flow rate and the density of condensate, and the time to saturation (when switched in to change of slope).

Molecular sieve dryer 250 is positioned to be switched in by valves 215 and 220 before the input stream reaches analyzer 100. The system controller in analyzer 100 responds and tracks loading of molecular sieve dryer 250.

Figure 3:
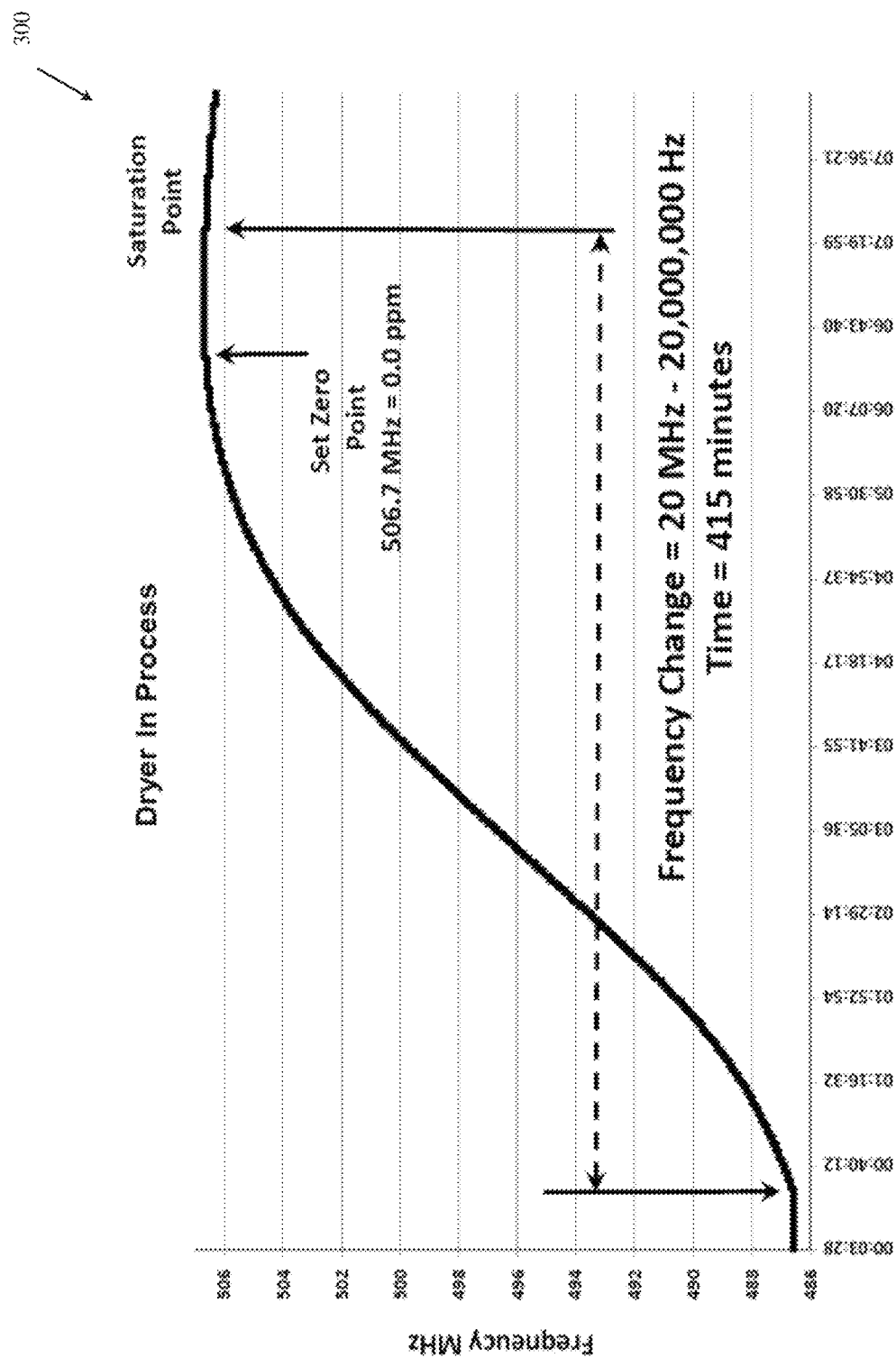
FIG. 3 is a diagram of actual molecular sieve dryer results.

FIG. 3 is a diagram of actual molecular sieve dryer results.

Figure 4:
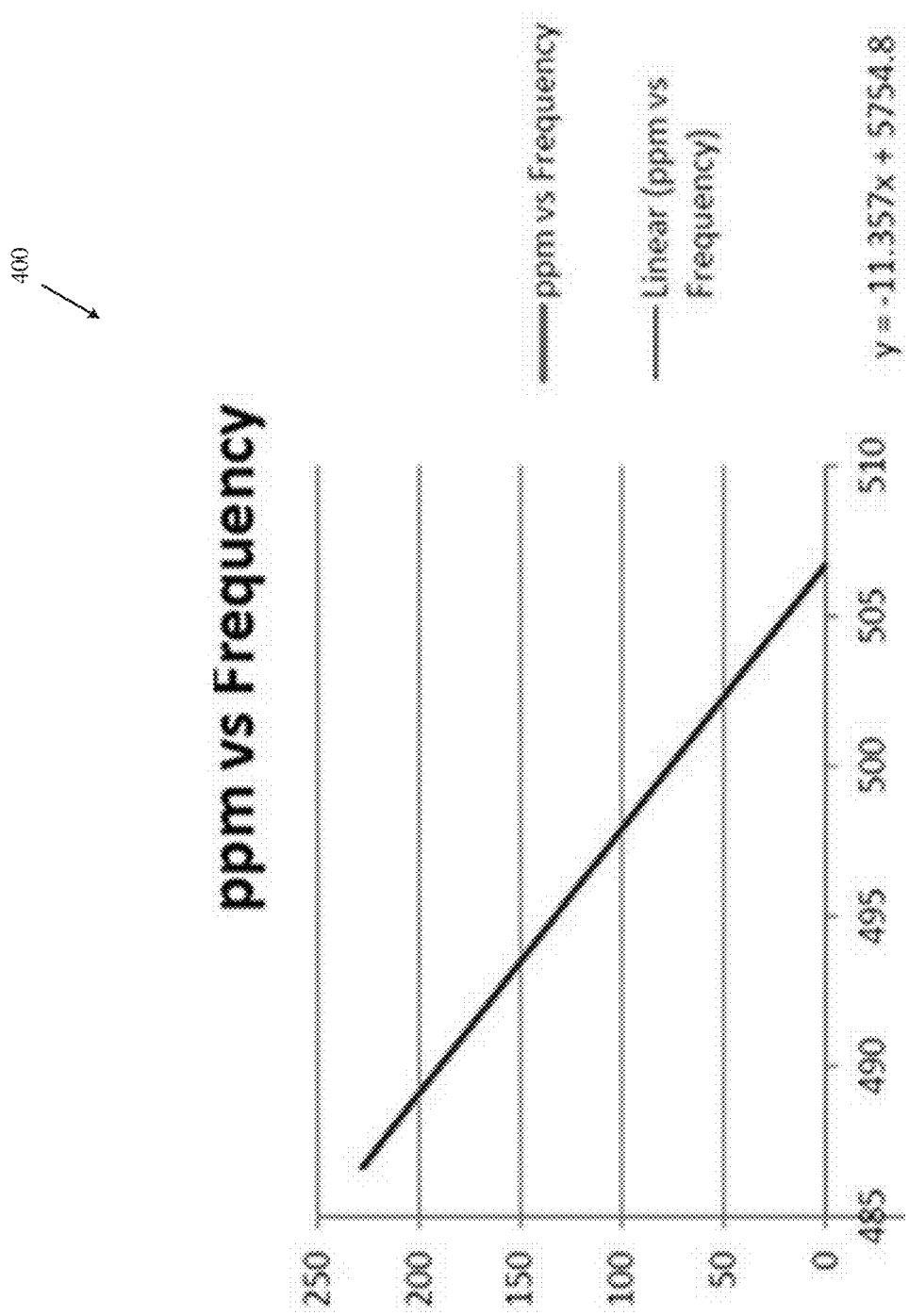
FIG. 4 illustrates a linear equation for the molecular sieve dryer.

FIG. 4 illustrates a linear equation for the molecular sieve dryer 250. The known characteristics of the process include: i) the process continues over time at a constant PPM level of water; ii) the flow rate is constant or can be integrated over time to know the total mass flow in the time interval up to when the molecular sieve is saturated; and iii) the density will be constant or flow-weighted and integrated over the time interval.

FIG. 3 shows the first point (Set Zero Point) where the molecular sieve in dryer 250 has allowed analyzer 100 to see zero water long enough to remove all water from the aluminum oxide beads within analyzer 100. The second inflection point (Saturation Point) after the zero point is where the molecular sieve material in dryer 250 begins to pass water back to analyzer 100. This means the molecular sieve material is saturated. The first point provides a method to determine a zero point or the intercept of an equation to define the change in frequency versus PPM level of water in analyzer 100. The second point, which assists in obtaining the slope of the linear equation in FIG. 4, may be obtained at the saturated molecular sieve frequency, time using the flow rate and density.

In FIG. 3, as the water is adsorbed by dryer 250, the permittivity measured by analyzer 100 changes. The initial PPM levels of 225 PPM are driven to near 0 PPM due to molecular sieve dryer 250 adsorbing the water from the incoming multiphase stream long enough for the aluminum oxide in pipe section 120 to de-adsorb all of the water. This zero point is at the inflection point in the response curve (i.e., the peak of the curve). Both solution water and free water are removed and the multiphase stream is sent to analyzer 100. The weight of the molecular sieve, the flow rate, the density and time are monitored until the analyzer shows an inflection point after a peak in the response curve. At this inflection point, the initial 1 kg of molecular sieve material has accumulated all the water it can, which is 22% of the mass (0.22 kg.) of the sieve material in dryer 250. Because the mass of the water (0.22 kg.) is precisely known, it can be compared to the total mass of the multiphase fluid measured by Coriolis meter 210 to determine a very precise measurement in PPM of water in the multiphase fluid. This result may then be compared to the results determined by analyzer 100 using the original factory calibration, thereby validating the operation of the PPM analyzer 100.

The process curve in FIG. 3 reflects a test that ran for 415 minutes during which dryer 250 saturated, with a flow rate of 3 liters per minute, a density of 705 kg/m$^3$, and an initial dry weight of molecular sieve equal to 1 kg. The frequency start point was 486.625 MHz and the endpoint was 506.7 MHz, corresponding to zero PPM in this case as shown in FIG. 3. When analyzer 100 responded later in time and showed a drop in frequency, this was the point of saturation of the molecular sieve in dryer 250. The total volume is 415 minutes times 3 liters/minute or 1,245 liters total. The volume of 1,245 liters equals 1.245 m$^3$ (i.e., 1,000 liters equals 1 m$^3$). Multiplying the volume of 1.245 m$^3$ by a density of 705 kg/m$^3$ equals 877.725 kg of multiphase liquid that passed through analyzer 100 in 415 minutes. Since it is known that the 1 kg of molecular sieve absorbed 0.22 kg of water, the slope ((506.7 MHz)×Slope+Intercept=0.22 kg/877.725 kg*1e−6) and intercept ((486.625 MHz)×Slope+ Intercept=0*1e−6) can be determined for PPM weight percentage. This may also be converted to volume percentage using the volumes instead of the mass. The resulting calibration for PPM volume value (vertical axis) is given by y=−11.208x+5679.1, where x is the frequency (horizontal axis).

Figure 5:
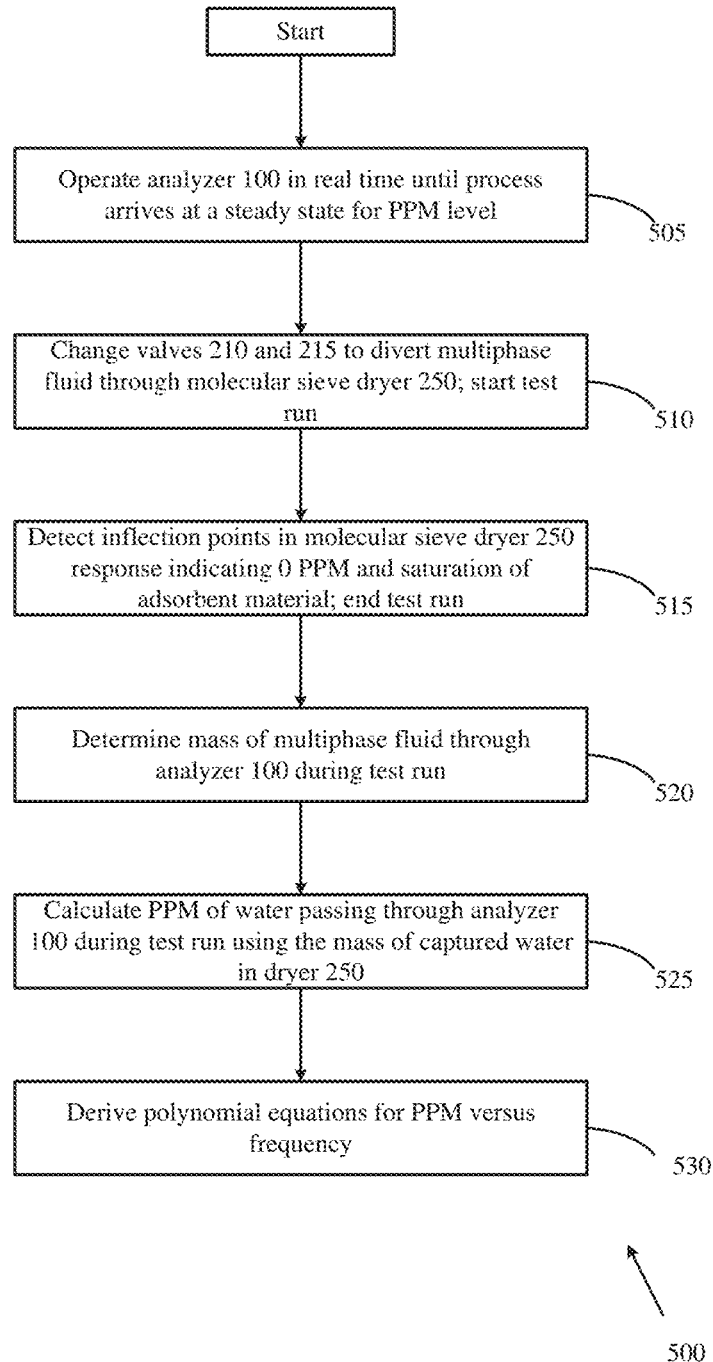
FIG. 5 is a flow diagram illustrating the operation of the PPM analyzer according to an embodiment of the disclosure.

FIG. 5 depicts flow diagram 500, which illustrates the operation of PPM analyzer 100 according to an embodiment of the disclosure. In 505, analyzer 100 operates in real time until process arrives at a steady state for PPM level. In 510, validation of the operation of analyzer 100 begins by changing valves 210 and 215 to divert the multiphase fluid through molecular sieve dryer 250 prior to entering the analyzer 100. The test run starts. In 515, analyzer 100 detects the inflection points in the response curve of molecular sieve dryer 250. The inflection points indicate: 1) the 0 PPM reference point and 2) the point where saturation of the adsorbent material has occurred. The test run ends.

Next, in 520, Coriolis meter 210 determines the total mass of the multiphase fluid through analyzer 100 during the test run. In 525, knowing the precise mass of the captured water in the adsorbent material and the total mass of the multiphase fluid through analyzer 100, the PPM of water that passed through analyzer 100 during test run is calculated. In 530, the internal system controller associated with analyzer 100 derive the polynomial equations for PPM versus frequency in FIG. 4.

The disclosed molecular sieve dryer 250 is relatively inexpensive compared to laboratory chemicals, personnel costs, and requirements for special lines from process, connectors, valves, and other equipment required for laboratory methods. Most off-line methods are hazardous to personnel. The disclosed apparatus and method reduce the exposure of personnel to hazardous solvents and hydrocarbons during the pulling of samples and laboratory procedures. In addition, the disclosed apparatus and method reduce the impact on the environment from disposal of these solvents. The disclose apparatus may be configured with a Coriolis meter for density and flow rate along with the analyzer electronics. Advantageously, the molecular sieve material may be regenerated (by heating) or thrown away after each test. The time required to calibrate and validate can be hours without personnel involvement except to interpret data.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. A system comprising:
   a parts-per-million (PPM) analyzer configured to analyze a multiphase fluid, the fluid comprising water, wherein the analyzer includes a mesh comprising first adsorbent materials that adsorb specific substances from the multiphase fluid;
   a mass meter configured to measure a mass of multiphase fluid passing through the PPM analyzer;
   a molecular sieve dryer comprising second adsorbent material configured to adsorb the water from the multiphase fluid; and
   a plurality of valves configured to couple the mass meter and the molecular sieve dryer to the PPM analyzer, wherein during routine operation, the valves direct the multiphase fluid through the PPM analyzer and wherein during a validation operation, the valves divert the multiphase fluid through the molecular sieve dryer prior to entering the PPM analyzer.

2. The system of claim 1, wherein the mass meter comprises a Coriolis meter.

3. The system of claim 1, wherein the second adsorbent material in the molecular sieve dryer has a known mass and adsorbs a known mass of water when saturated.

4. The system of claim 3, further comprising a system controller configured to determine a zero reference point in an output of the analyzer, the zero reference point indicating that during the validation operation, the multiphase fluid from the molecular sieve dryer has removed substantially all of the water associated with the first adsorbent materials in the mesh.

5. The system of claim 4, wherein the system controller is further configured to determine a saturation point in the output of the analyzer, the saturation point indicating that during the validation operation, the second adsorbent material associated with the molecular sieve dryer has become saturated.

6. The system of claim 5, wherein the system controller uses the known mass of water when the second adsorbent material is saturated to verify the parts-per-million of water that passed through the PPM analyzer during the validation operation.

7. A method of validating the operation of a parts-per-million (PPM) analyzer configured to analyze a multiphase fluid, the fluid comprising water, the method comprising:
   during a routine operation, directing the multiphase fluid through the PPM analyzer, wherein the analyzer includes a mesh comprising first adsorbent materials that adsorb specific substances from the multiphase fluid;
   during a validation operation, diverting the multiphase fluid through a molecular sieve prior to entering the PPM analyzer, the molecular sieve comprising a second adsorbent material that adsorbs the water from the multiphase fluid;
   measuring the mass of multiphase fluid passing through the PPM analyzer during the validation operation; and
   determining a zero reference point in an output of the analyzer, the zero reference point indicating that during the validation operation, the multiphase fluid from the molecular sieve dryer has removed substantially all of the water associated with the first adsorbent materials in the mesh.

8. The method of claim 7, further comprising:
determining a saturation point in the output of the analyzer, the saturation point indicating that during the validation operation, the second adsorbent material associated with the molecular sieve dryer has become saturated.

\* \* \* \* \*